(12) United States Patent
Tan et al.

(10) Patent No.: US 11,536,712 B2
(45) Date of Patent: Dec. 27, 2022

(54) HEALTH SEAT FOR TOILETS AND BIDETS

(71) Applicant: Kohler Co., Kohler, WI (US)

(72) Inventors: Luncheak Tan, Shanghai (CN);
Chinghua Chen, Shanghai (CN)

(73) Assignee: Kohler Co., Kohler, WI (US)

( * ) Notice: Subject to any disclaimer, the term of this patent is extended or adjusted under 35 U.S.C. 154(b) by 627 days.

(21) Appl. No.: 16/425,473

(22) Filed: May 29, 2019

(65) Prior Publication Data

US 2019/0369085 A1    Dec. 5, 2019

(30) Foreign Application Priority Data

May 31, 2018  (CN) .......................... 201810552190.6
May 31, 2018  (CN) .......................... 201820840264.1

(51) Int. Cl.
| | |
|---|---|
| *G01N 33/493* | (2006.01) |
| *G01N 1/10* | (2006.01) |
| *E03D 9/00* | (2006.01) |
| *E03D 5/02* | (2006.01) |
| *E03D 5/00* | (2006.01) |

(52) U.S. Cl.
CPC ............. *G01N 33/493* (2013.01); *E03D 5/00* (2013.01); *E03D 5/022* (2013.01); *E03D 9/00* (2013.01); *G01N 1/10* (2013.01)

(58) Field of Classification Search
CPC .......... E03D 5/00; E03D 9/00; G01N 33/493; G01N 1/10; A61B 10/00
USPC ......................................................... 600/573
See application file for complete search history.

(56) References Cited

U.S. PATENT DOCUMENTS

| | | | |
|---|---|---|---|
| 3,465,968 A | 9/1969 | Halpern | |
| 5,073,500 A * | 12/1991 | Saito ........................ | A61B 5/20 |
| | | | 4/300 |
| 5,730,149 A * | 3/1998 | Nakayama ........... | G01N 33/493 |
| | | | 600/584 |
| 10,921,310 B2 * | 2/2021 | Mostafa ................. | G01N 21/77 |
| 11,123,049 B2 * | 9/2021 | Kramer .............. | B01L 3/50853 |
| 2006/0226255 A1 | 10/2006 | Deboer et al. | |
| 2009/0216099 A1 * | 8/2009 | Kim ........................ | A61B 5/25 |
| | | | 600/509 |
| 2017/0055884 A1 * | 3/2017 | Takeuchi ............... | A61B 5/702 |
| 2017/0189919 A1 | 7/2017 | Mei | |
| 2018/0184906 A1 * | 7/2018 | Prokopp .............. | A61B 5/4343 |

FOREIGN PATENT DOCUMENTS

| | | |
|---|---|---|
| CN | 101945708 | 1/2011 |
| CN | 102041844 | 5/2011 |
| CN | 104822462 | 8/2015 |

(Continued)

OTHER PUBLICATIONS

English Machine translation of CN106567435A printed Feb. 25, 2022 (Year: 2022).*

(Continued)

*Primary Examiner* — Christine J Skubinna
(74) *Attorney, Agent, or Firm* — Lempia Summerfield Katz LLC

(57) ABSTRACT

An intelligent toilet that includes a toilet base having a bowl, a seat assembly comprising a seat, and a urine collection system integrated with the seat assembly, wherein the urine collection system includes an analyzer that is configured to test urine from a user and provide output health data of the user.

22 Claims, 10 Drawing Sheets

(56) References Cited

FOREIGN PATENT DOCUMENTS

| | | |
|---|---|---|
| CN | 104912166 | 9/2015 |
| CN | 105971082 A | 9/2016 |
| CN | 205983742 | 2/2017 |
| CN | 106567435 | 4/2017 |
| DE | 39 07 379 A1 | 3/1989 |
| DE | 10 2012 018 878 | 3/2014 |
| JP | H07-234178 | 9/1995 |

OTHER PUBLICATIONS

English Machine translation of CN105971082A printed Feb. 25, 2022 (Year: 2022).*
CN Second Office Action on CN Patent Application No. 201920910103 dated May 31, 2021 (10 pages).
Indian First Examination Report on IN Patent Application No. 201914033677 dated Oct. 14, 2020 (6 pages).
CN First Office Action on Appl No. 201820840264.1 dated Dec. 18, 2018 (3 pages).
CN Office Action on Appl. No. 201810552190.6 dated Jul. 1, 2020 (24 pages).

* cited by examiner

HEALTH SEAT FOR TOILETS AND BIDETS

CROSS REFERENCE TO RELATED APPLICATIONS

This application claims priority to and the benefit of Chinese Priority Application Nos. 201810552190.6 and 201820840264.1, both of which were filed on May 31, 2018. The entire disclosures of the foregoing applications, including the specifications, drawings, claims and abstracts, are incorporated herein by reference in their entireties.

TECHNICAL FIELD

This application generally relates to the field of toilets or bidets. More specifically, this application relates to intelligent toilets or bidets that provide functions to a user in response to data collected in relation to the user or user input. For example, the toilets/bidets can collect and analyze urine samples to provide a user with personal health information, such as through a mobile application.

BACKGROUND

Often urinalyses are conducted to provide a user with an indication of various health concerns or statistics that may otherwise remain undetected. For example, a urinalysis may indicate to a user if she is dehydrated, the timing of her menstrual cycle, or if she exhibits symptoms of various diseases based on the protein or ketone levels, or urine specific gravity of the sample. However, while urinalyses are beneficial for the detection and tracking of health concerns, people rarely have the ability to conduct and analyze such an analysis in their own home. Commonly, urinalyses are performed under supervision of a physician or other medically trained person(s). This requires time and can be costly. Thus, there is a need to provide individuals with greater access to health information without having to visit a physician.

SUMMARY

At least one embodiment of this application relates to an intelligent toilet that includes a toilet base having a bowl, a seat assembly comprising a seat, and a urine collection system integrated with the seat assembly. The urine collection system includes an analyzer that is configured to test urine from a user and provide output health data of the user.

At least one embodiment of this application relates to an intelligent toilet that includes a toilet base, a urine collection system, and platform. The toilet base has a body and a bowl in the body. The urine collection system has a valve, which is integrated into an opening in the bowl, and an analyzer, which is located in the toilet base and is configured to analyze urine from a user and provide output health data of the user. The platform extends from a lower front of the body and includes at least one of a foot warmer, a heart rate sensor that measures a heart rate of the user, and a scale that measures a weight of the user.

At least one embodiment of this application relates to an intelligent toilet that includes a toilet base; a seat assembly, an analyzer, a posture module, and a control module. The seat assembly has a seat and a lid that are rotatably coupled to the toilet base. The analyzer is integrated with at least one of the toilet base and the seat assembly, and the analyzer tests urine from a user and provides output health data of the user. The posture module has a sensor that measures and outputs a signal of a posture of the user when seated on the seat. The control module receives the signal and compares the measured posture to a threshold range, so that a first posture control signal is emitted in response to the measured posture being within the threshold range and a second posture control signal is emitted in response to the measured posture being outside of the threshold range.

This summary is illustrative only and is not intended to be in any way limiting. Other aspects, inventive features, and advantages of the devices and/or processes described herein, as defined solely by the claims, will become apparent in the detailed description set forth herein, taken in conjunction with the accompanying figures, wherein like reference numerals refer to like elements.

BRIEF DESCRIPTION OF THE DRAWINGS

Exemplary embodiments are described herein with reference to the following drawings.

FIG. 21 is a partial cutaway perspective view of a portion of the toilet shown in

FIG. 18.

DETAILED DESCRIPTION

Before turning to the figures, which illustrate the exemplary embodiments in detail, it should be understood that the present disclosure is not limited to the details or methodology set forth in the description or illustrated in the figures. It should also be understood that the terminology used herein is for the purpose of description only and should not be regarded as limiting Turning to the figures, disclosed in this application are embodiments of toilets that provide a user with mechanisms and methods of tracking and improving their overall health, while improving convenience and comfort while using the toilets.

Urine Collection/Analysis Systems

Figure 1:
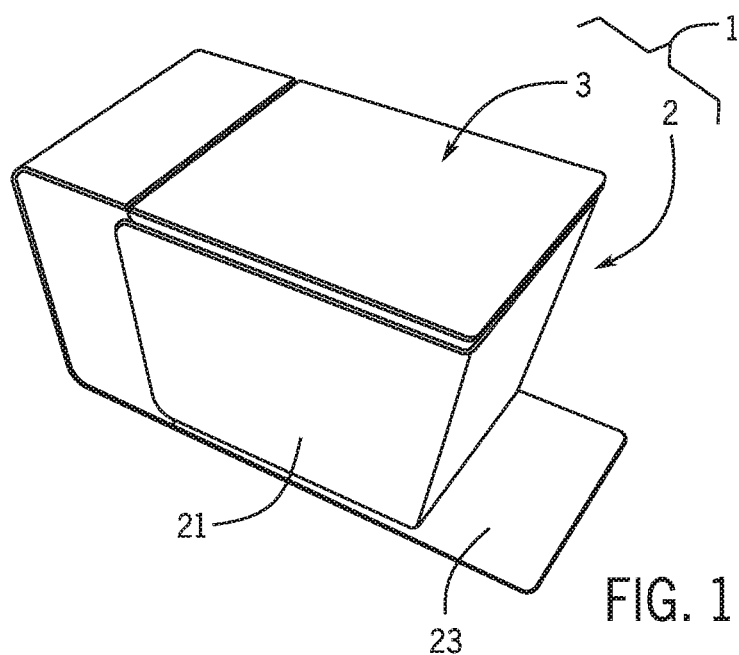
FIG. 1 is a perspective view of an intelligent toilet, according to an exemplary embodiment of this application.
Figure 2:
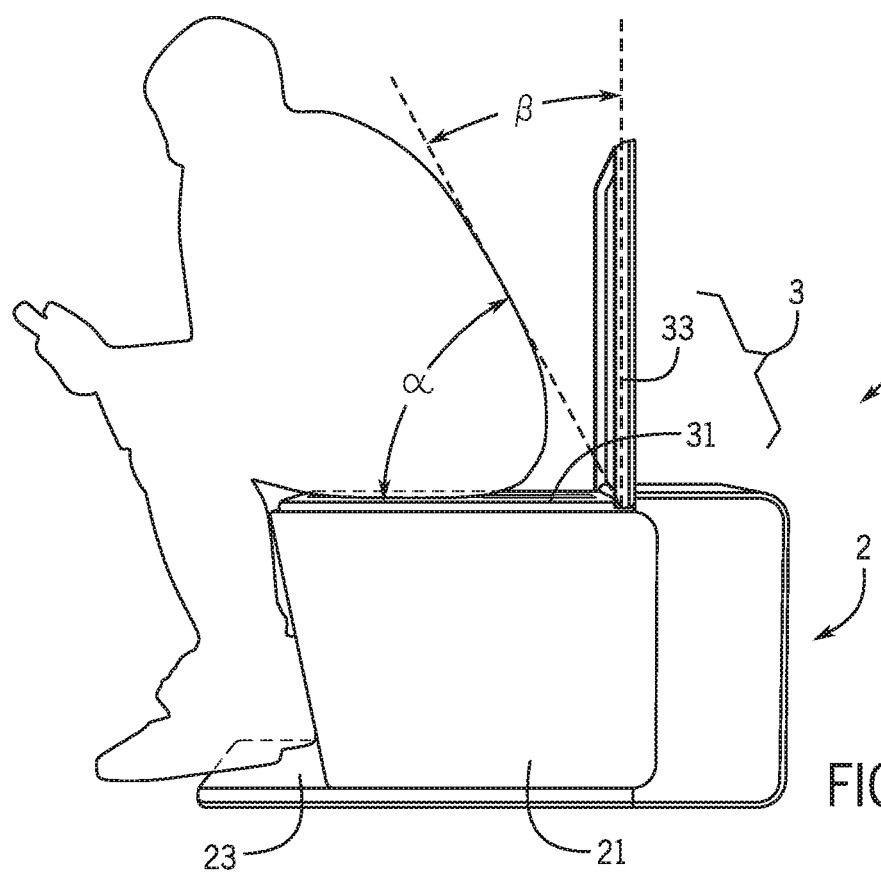
FIG. 2 is a side perspective view of a user on the toilet shown in FIG. 1, which includes a foot warmer and posture reminder.

FIGS. 1 and 2 illustrate an intelligent toilet 1 (e.g., smart toilet, etc.) having a toilet base 2 and a seat system 3 rotatably coupled to the toilet base 2. The illustrated toilet base 2 includes an outer body 21 (e.g., a shell, casing, skirting, etc.) and a foot warmer 23 disposed at and extending from a front bottom portion of the outer body 21. As shown in FIG. 2, the seat system 3 includes a seat 31 and a lid 33 (e.g., cover) that are independently rotatably about the toilet base 2. The illustrated toilet 1 is configured to monitor the posture of a user on the toilet 1 and alert the user if the posture is outside of a healthy (e.g., ergonomic) range, which is discussed below in the "Posture Reminder" section. The toilet 1 also includes a system for collecting and analyzing urine. For example, the system can receive and maintain urine test strips within the toilet, where each test strip is directed into a user's stream of urination for collection, then is analyzed within the system to produce health information of the user. After analyzation, the used test strip can be discarded. These aspects are discussed below in more detail. It is noted that the term "toilet" as used herein includes toilets, bidets, and the like.

Figure 6:
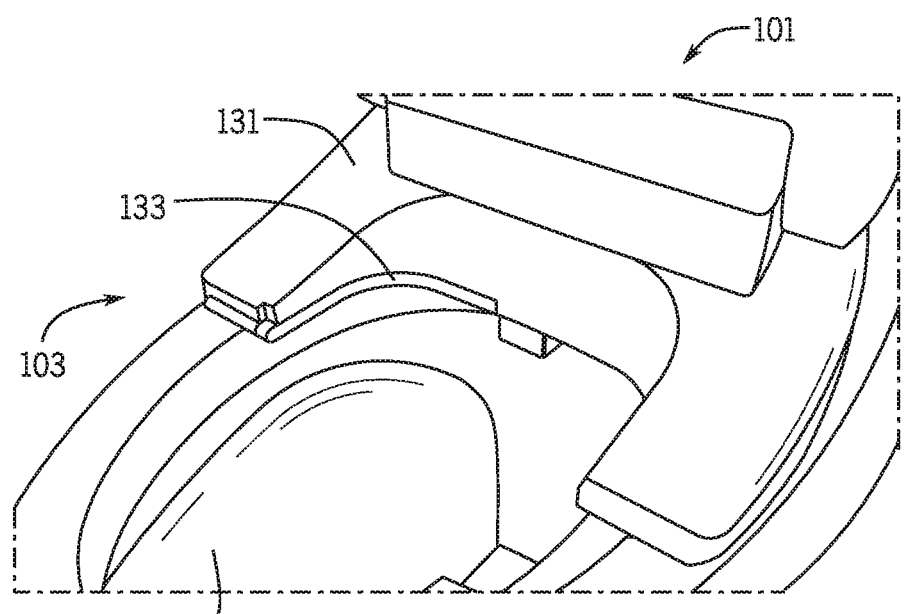
FIG. 6 is a perspective view of an exemplary embodiment of a toilet having a urinalysis tester shown in a non-use position.
Figure 7:
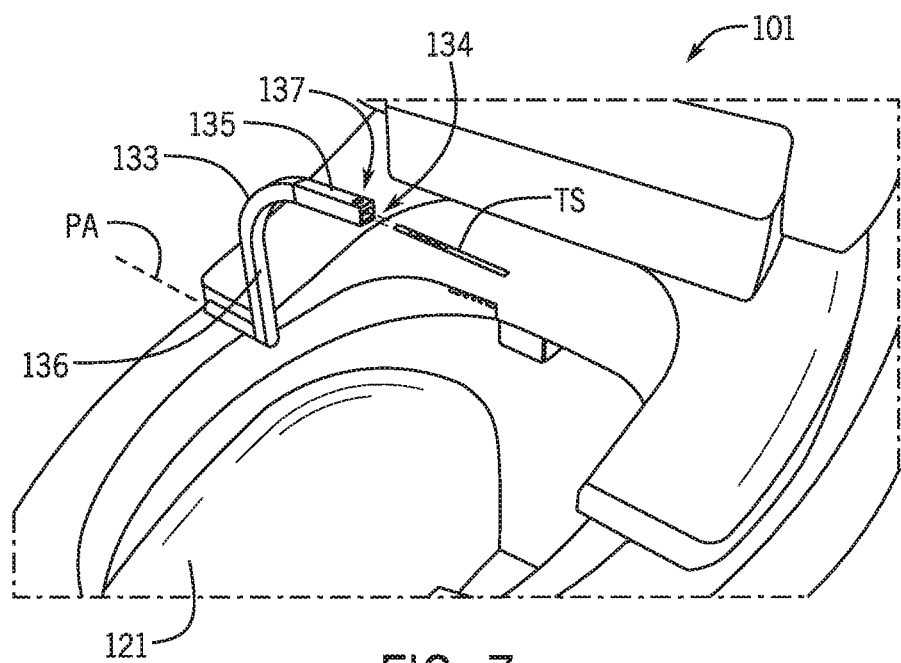
FIG. 7 is a perspective view of the toilet shown in FIG. 6 with the urinalysis tester shown in a use position.
Figure 8:
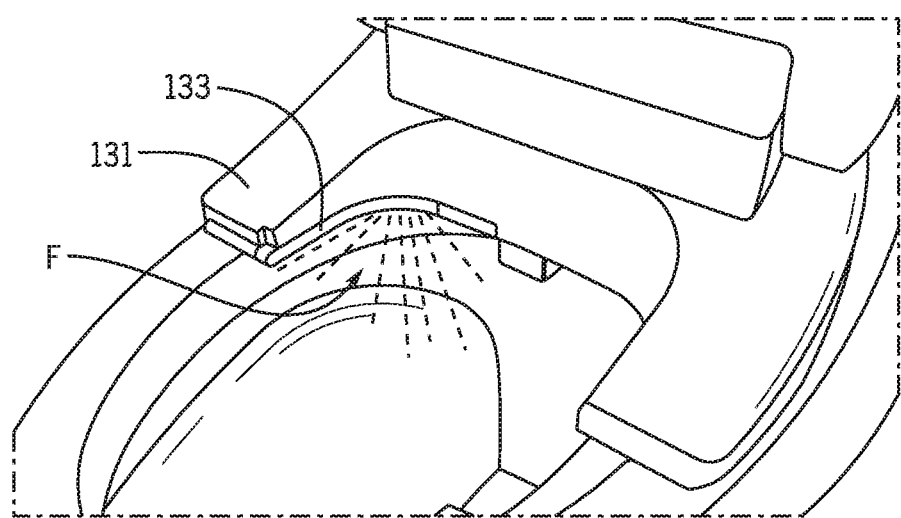
FIG. 8 is a perspective view of the toilet shown in FIG. 6 with the urinalysis tester being washed.

FIGS. 6-8 illustrate an exemplary embodiment of a toilet 101 having a system for collecting and analyzing urine integrated with the seat assembly 103. The system includes a base 131, which can be part of a seat or separate from a seat, such as underneath a seat. The base 131 is shown mounted on a top surface of a bowl 121. The system includes an arm 133 that is rotatably coupled to the base 131 about a pivot axis PA, so that the arm 133 is movable into multiple positions. FIG. 6 illustrates a non-use (e.g., stored, retracted, etc.) position of the arm 133, in which the arm 133 nests within a recess 132 in a forward and inward facing portion of the base 133. FIG. 7 illustrates a first use position of the arm 133, in which the arm 133 extends upward and inward relative to a rim (e.g., a top surface) of the bowl 121. In the first use position, a test strip TS can be inserted into a receiving aperture 134 in the arm 133, such as a distal end 135 relative to a pivot end 136 of the arm 133, for analysis by an analyzer of the system that analyzes urine on the test strip TS. The illustrated aperture 134 is in an end surface of the distal end 135. The analyzer can be located in the base (similar to the analyzer 450 discussed below), in other parts of the base (e.g., proximate the pivot end 136), or in the arm 133.

The system of toilet 101 can be configured to receive a clean test strip TS (i.e., one that has not yet been urinated on) prior to or after the arm 133 has moved into a position (e.g., first use position, second use position) so a user can urinate over the distal end 135 to collect a urine sample on the test strip, such as through one or more holes 137 in the distal end 135. Notably, the second use position can be one or more different locations, which can be tied to a specific user or to the gender of a non-specific user, such as after the toilet 101 has identified a specific user or the gender of a non-specific user. Alternatively, the system can be configured to receive a test strip TS that has already been urinated on, then analyze the urine. Either way, the system can output health data of the user (e.g., data OHD), as discussed below. The system can then discard the used test strip, such as by discarding it into the bowl 121 to be flushed out, holding it in a compartment to be emptied by the user, discarded by the user, or in another suitable manner. For example, the system can utilize fluid pressure (e.g., hydraulic pressure), such as using water, to force the test strip TS out of the receiving aperture 134 in an arm 133 and into the bowl to be flushed away during the next flush cycle of the toilet.

The system of toilet 101 can provide a cleaning cycle, which can be automatically initiated (e.g., by the system after each use) or initiated by a user, such as to ensure that one or more surfaces of the system is sanitized and free from any contaminants or bacteria. As shown in FIG. 8, the arm 133 is washed by a fluid F (e.g., clean water from a tank or water inlet, water and a cleaning chemical, etc.) during a cleaning cycle, such as after the strip has been discarded. The fluid can be flushed by passing the fluid through the arm 133 and/or over the arm 133, such as from one or more nozzle(s) of the system, during such a cleaning cycle. In addition to or alternatively, the system can include other cleaning methods, such as exposing the arm 133 to UV light, high temperatures, or other similar cleansers. The toilet 101 can be configured to clean other parts of the toilet after the strip has been discarded, such as the toilet bowl. See, e.g., U.S. Patent Application Publication No. 2017/0058500 (to Garrels et al.) for examples of additional cleaning devices that can be incorporated with the systems of this application.

Figure 9:
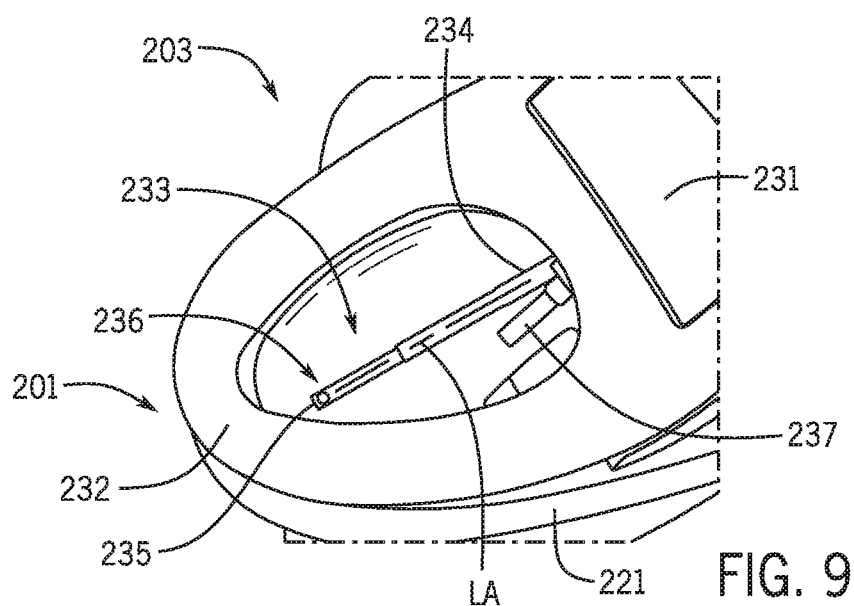
FIG. 9 is a perspective view of another toilet having a urinalysis tester.

FIG. 9 illustrates another exemplary embodiment of a toilet 201 having a system for collecting and analyzing urine integrated with the seat assembly 203. The illustrated seat assembly 203 includes a base 231, which is mounted to the bowl 221, a seat 232 rotatably coupled to the base 231 for supporting a user in a down or seated position, and an arm 233 extending from the base 231 toward a front part of the bowl 221. The arm 233 can be a cantilevered rod mounted to and extending from a forward facing surface of the base 231. The illustrated arm 233 has a first end 234 coupled (e.g., fixedly coupled, moveably coupled) to the base 231 and a second distal end 235, which can be configured to receive a test strip TS, such as through a receiving aperture. One or more than one upwardly facing hole 236 can be located proximate the distal end 235, such as to receive urine for collection on a test strip TS in the arm 233. The arm 233 can be moveable, such as telescopically to reposition the distal end 235 along a longitudinal axis LA of the arm 233 relative to the fixed end 234, and/or pivotally, such as to swivel the arm 233 in a horizontal plane and/or a vertical plane and/or to freely rotate (e.g., through a ball joint) the arm 233 (e.g., up-and-down, laterally, etc.). The telescopic arm 233 allows a user to reposition the second distal end 235 containing the test strip TS relative to the first end 234 to a position that is more suitable/ergonomic for the user to urinate over the test strip. Once the test strip contains urine, an analyzer of the system analyzes the urine on the test strip and outputs health data of the user. The analyzer can be integrated with (e.g., located within) the arm 233, in the base 231 (similar to the analyzer 450), or located elsewhere on the toilet 101. The seat assembly 203 can, optionally, be integrated with a bidet wand 237, as shown in FIG. 9, which is configured to wash a user of the toilet. The bidet wand 237 can also be configured to wash the arm 233, such as during a cleaning cycle of the system.

Figure 10:
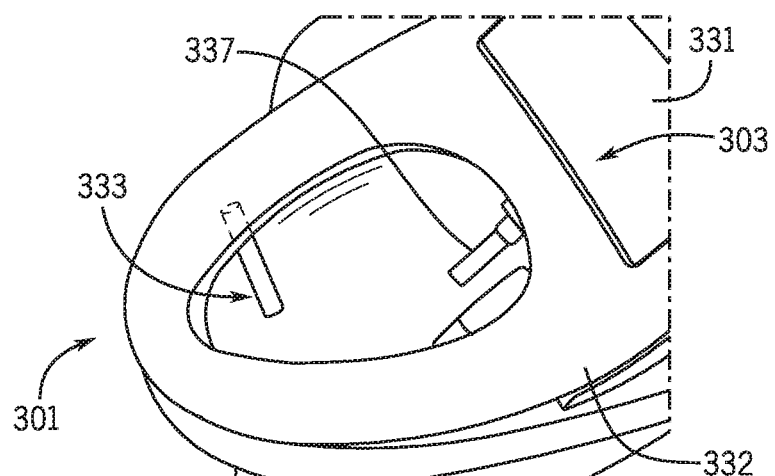
FIG. 10 is a perspective view of another toilet having a urinalysis tester.

FIG. 10 illustrates another exemplary embodiment of a toilet 301 having a system for collecting and analyzing urine integrated with the seat assembly 303, which is similar to the assembly 203, except the arm 333 of the assembly 303 extends from a side of the seat 332 or a side of the base 331 to which the seat 332 is pivotally coupled to (rather that from a rear portion of the base). The arm 333 can be moveable, such as in the same ways discussed above regarding the arm 233. Further, the arm 333 is configured to receive a test strip TS, such that an analyzer of the system analyzes the urine on the test strip and outputs health data of the user. Similarly, the seat assembly 303 can, optionally, be integrated with a bidet wand 337 (also shown in FIG. 10) that is configured to wash a user of the toilet and/or the arm 333.

For some users, the configurations shown in FIGS. 9 and 10 having arms, which may be stationary or moveable, provide an easier or more ergonomic location for a user to urinate over to expose the test strip to the user's urine. However, testing has demonstrated that in addition to different gendered users urinating in different locations/areas of the bowl (e.g., urine from seated males most commonly contacts the front-center of the bowl, whereas urine from seated females most commonly contacts the bowl more centrally in both fore-and-aft and lateral directions), different users of the same gender often urinate in different locations/areas of the bowl. Hence, it would be difficult for a fixed and stationary device to capture urine from all potential users, absent discomfort and inconvenience to some or many users. Accordingly, a urine collector mechanism that allows the collection device to be decoupled from the toilet to collect the urine sample, and then recoupled after collection to analyze the sample offers added flexibility and comfort to some or many users.

Figure 11:
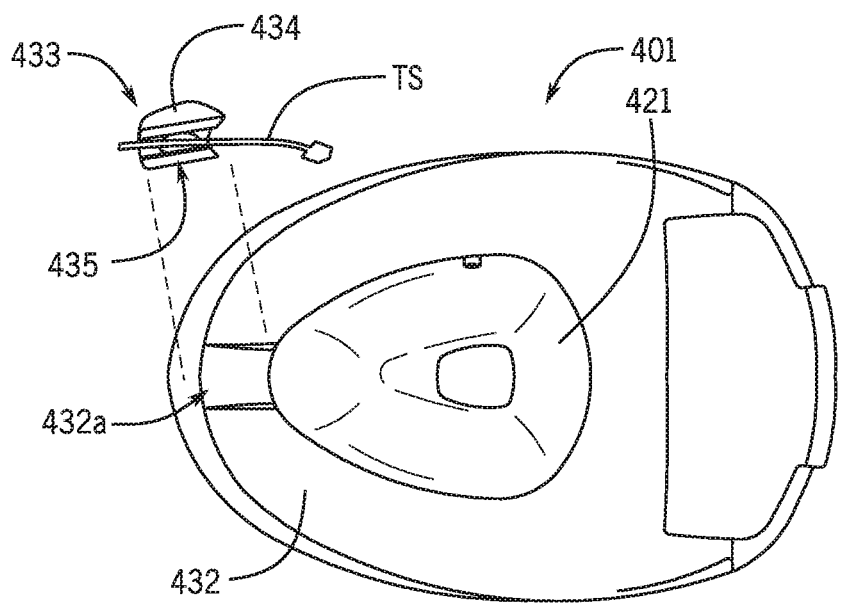
FIG. 11 is a top perspective view of another toilet having a urinalysis tester having a detachable collector shown detached from the seat.
Figure 12:
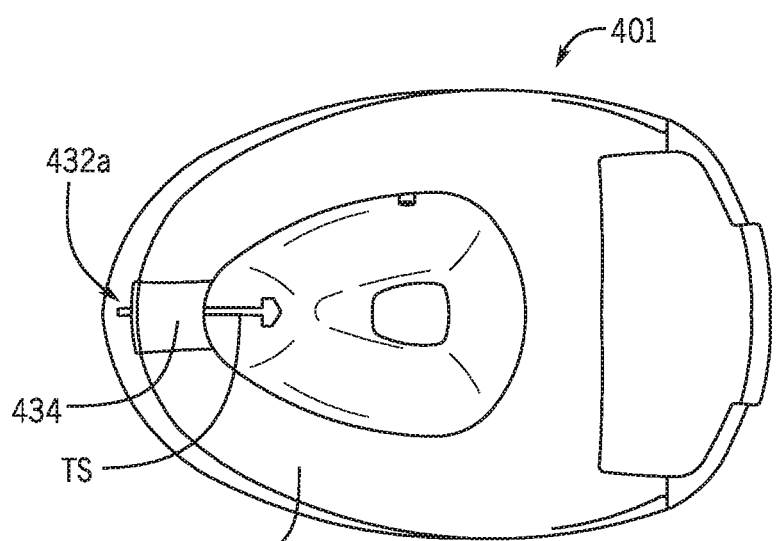
FIG. 12 is a top perspective view of the toilet shown in FIG. 11 with the detachable collector shown attached to the seat.

FIGS. 11 and 12 illustrate another exemplary embodiment of a toilet 401 having a urine collector mechanism that can be decoupled from (and recoupled back to) the toilet 401. The illustrated toilet 401 includes a seat 432 having a notch 432a in a forward and upward portion for removably (e.g., detachably) receiving a mount 434 of a urine collection mechanism 433. The illustrated notch 432a does not extend all the way through the thickness of the seat 432 (e.g., moving from top to bottom). The mount 434 is shaped to complement the notch 432a so that when the mount 434 is coupled to the seat 432, the seat 432 looks whole (i.e., the notch 432a is filled by the mount 434). As shown in FIG. 11, the mount 434 can be detached from the seat 432, such as to reposition a test arm or add/remove a test strip TS depending on the configuration of the urine collection mechanism 433. The illustrated mount 434 includes an aperture 435 (e.g., recess, channel, etc.) to receive part of a test strip TS. Upon inserting a test strip TS into the aperture 435, the mount 434 can be placed in the notch 432a, as shown in FIG. 12, such that a distal end of the test strip TS extends rearward and inward towards the center of the bowl 421. Hence, a user can urinate on the test strip TS (e.g., the distal end thereof) to collect a urine sample on the test strip TS for analysis in an analyzer. For some users, the urine collection mechanism 433 shown in FIGS. 11 and 12 may provide a more comfortable and effective location for the user to collect a urine sample on the test strip TS, as the test strip TS will be located closer to the front-central part of the bowl 421. It is noted that the notch 432a and the mount 434 can be relocated elsewhere on the seat 432, such as off to one side. The seat 432 can include several notches (e.g., one in the front, one in the side) to provide additional flexibility with respect to the location of attaching a test strip TS. According to another embodiment, an arm (e.g., similar to the arm 233, 333, etc.) can be coupled to the mount 434 and extend inwardly, where the arm is configured to receive a test strip TS through a receiving aperture (e.g., the receiving aperture 134) or to support a test strip TS externally on the arm.

Figure 13:
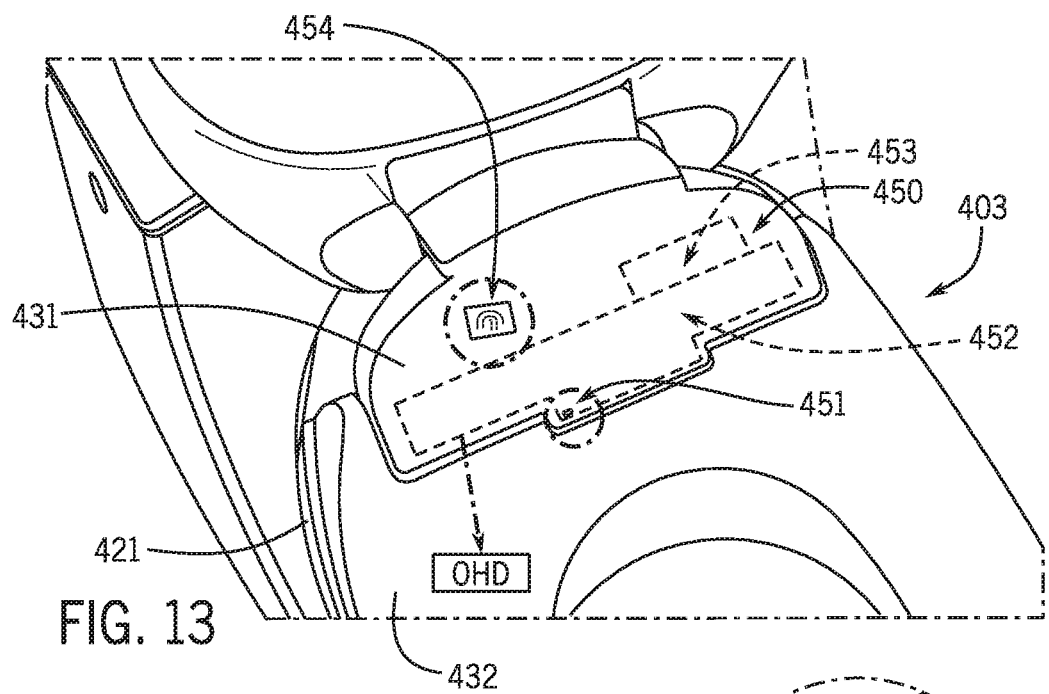
FIG. 13 is a perspective view of yet another toilet having a urinalysis tester.
Figure 15:
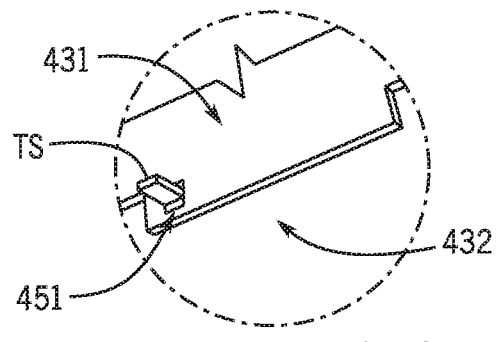
FIG. 15 is a detail view of a test strip in an inlet opening in an analyzer of the toilet shown in FIG. 13.

Once a urine sample is collected (e.g., on a test strip TS), the urine can be analyzed in an analyzer. FIG. 13 illustrates an exemplary embodiment of an analyzer 450 integrated into a base 431 of the seat assembly 403, which can be used with the toilet 401 or any other toilet disclosed herein. The base 431 can be configured according to other bases described herein, such as to directly couple to a portion of the bowl 421. As shown best in FIG. 15, an inlet opening 451 in the base 431 and/or the analyzer 450 is provided to receive the test strip TS containing the urine sample. Once the test strip TS is inserted into the inlet opening 451, an internal processor 452 (e.g., a microprocessor) of the analyzer 450 performs the analysis on the sample and provides output health data OHD (e.g., data OHD) of the user.

Figure 5:
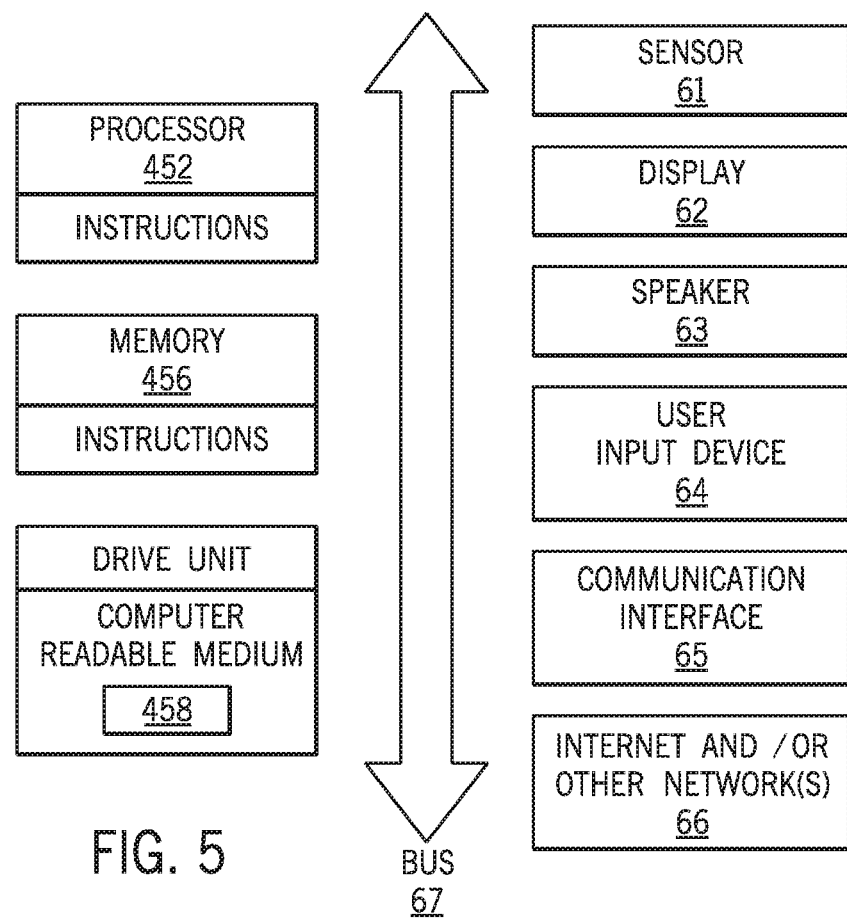
FIG. 5 is a diagram of an exemplary embodiment of a controller for use with a toilet, such as the toilet shown in FIG. 1.

The data OHD is shown in FIG. 13 as a schematic box (containing "OHD") that is connected to the processor 452 via a phantom line illustrating that the data OHD can be transmitted through a wire, wirelessly, or in any suitable manner. For example, the OHD can be transmitted through a communications interface 65 and/or a network 66 (FIG. 5). The OHD, as well as other information obtained and/or used by the toilet can be retained in a memory 456, which can be accessible by the processor 452. For example, the control system depicted schematically in FIG. 5 can be used to access, store, and transmit the OHD. As shown, the various components of the control system can communicate with one another using a bus 67. For example, the control system can connect to a workstation, another external device, such as a user input device 64 (e.g., remote control, on toilet controller, smartphone or like device, etc.), and/or one or more sensors 61, displays 62 and/or speakers 63. A drive unit can be provided to receive and read non-transitory computer media 161 having instructions 162. The processor 452 can perform instructions, which can be stored in the memory 456. The processor 452 can be or include a general purpose or specific purpose processor, an application specific integrated circuit (ASIC), one or more programmable logic controllers (PLCs), one or more field programmable gate arrays (FPGAs), a group of processing components, or other suitable processing components. The processor 452 can execute computer code, instructions stored in the memory 456, and/or code/algorithms received from other computer readable media (e.g., embedded flash memory, local hard disk storage, local ROM, network storage, a remote server, etc.). The processor 452 can be a single device or combination of multiple devices, such as associated with a network, distributed processing, or cloud computing.

The memory 456 can include one or more devices (e.g., memory units, memory devices, storage devices, etc.) for storing data and/or computer code for completing and/or facilitating the various processes described in the present disclosure. The memory 456 can include random access memory (RAM), read-only memory (ROM), hard drive storage, temporary storage, non-volatile memory, flash memory, optical memory, or any other suitable memory for storing software objects and/or computer instructions. The memory 456 can include database components, object code components, script components, or any other type of information structure for supporting the various activities and information structures described in the present disclosure. The memory 456 can be communicably connected to the processor 452 via a processing circuit and can include computer code for executing one or more processes described herein. For example, the memory 456 can include graphics, web pages, HTML files, XML files, script code, shower configuration files, or other resources for use in generating graphical user interfaces for display (e.g., on a display 62) and/or for use in interpreting user interface inputs to make command, control, or communication decisions.

In addition to ingress ports and egress ports, the communication interface 65 can include any operable connection. An operable connection can be one in which signals, physical communications, and/or logical communications can be sent and/or received. An operable connection can include a physical interface, an electrical interface, and/or a data interface. The communication interface 65 can be connected to a network. The network can include wired networks (e.g., Ethernet), wireless networks, or combinations thereof. The wireless network can be a cellular telephone network, an 802.11, 802.16, 802.20, or WiMAX network, a Bluetooth pairing of devices, or a Bluetooth mesh network. Further, the network can be public (e.g., the Internet), private (e.g., an intranet), or combinations thereof, and can utilize any suitable networking protocol (e.g., TCP/IP based networking protocols).

The computer-readable medium 458 (e.g., the memory 456, drive unit 160, etc.) can be a single medium or include multiple media, such as a centralized or distributed database, and/or associated caches and servers that store one or more sets of instructions. The term "computer-readable medium" shall include any medium that is capable of storing, encoding or carrying a set of instructions for execution by a processor or that cause a computer system to perform any one or more of the methods or operations disclosed herein, such as, but not limited to, a solid-state memory (e.g., a memory card or other package that houses one or more non-volatile read-only memories), a random access memory or other volatile re-writable memory, a magneto-optical or optical medium (e.g., a disk or tapes or other storage device to capture carrier wave signals such as a signal communicated over a transmission medium). A digital file attachment to an e-mail or other self-contained information archive or set of archives can be considered a distribution medium that is a tangible storage medium. Accordingly, the disclosure is considered to include any one or more of a computer-readable medium or a distribution medium and other equivalents and successor media, in which data or instructions can be stored. The computer-readable medium can be non-transitory, which includes all tangible computer-readable media.

It is noted that dedicated hardware implementations, such as application specific integrated circuits, programmable logic arrays and other hardware devices, can be constructed to implement one or more of the methods described herein. Applications that can include the apparatus and systems of various embodiments can broadly include a variety of electronic and computer systems. One or more embodiments described herein can implement functions using two or more specific interconnected hardware modules or devices with related control and data signals that can be communicated between and through the modules, or as portions of an application-specific integrated circuit. Accordingly, the present system encompasses software, firmware, and hardware implementation.

The data OHD can be transmitted through the system to other components/parts of the toilet, which may be physically and/or electronically coupled to the toilet or may be remote from the toilet altogether, such as to a smart device (e.g., phone, tablet, etc.). The analyzer 450 (e.g., the microprocessor 452) can be powered electrically by an internal battery 453 and/or an external electric power supply (not shown). For example, the toilet 1 can connect to a standard residential power outlet (e.g., 120 V at 60 Hz, 220V at 50 Hz, etc.), a power generator, or other power source (e.g., other batteries, capacitors, etc.).

Figure 14:
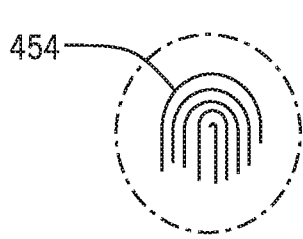
FIG. 14 is a detail view of a fingerprint scanner on the toilet shown in FIG. 13.
Figure 16:
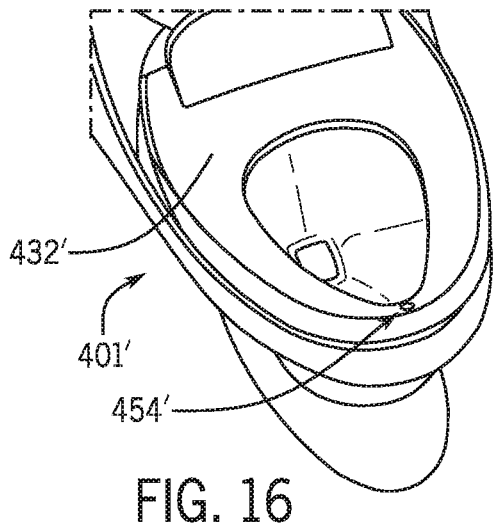
FIG. 16 is a perspective view of another toilet having a fingerprint scanner.

The toilets having urine collection devices (e.g., the arms 133, 233, 333; the urine collection mechanism 433, etc.) can include user identification features, which can be integrated with the urine collection device or other components of the toilet. FIGS. 13 and 14 illustrate a fingerprint scanner 454 located on the base 431 of the seat assembly 403. The intelligent toilet can identify the user based on a scan of the user's fingerprint on the fingerprint scanner 454. In this way, the toilet can collect, store (e.g., record, etc.) and/or output data OHD specific to the identified user based on, for example, a urine sample tested by the toilet. Accordingly, the intelligent toilet can track data OHD for multiple users (e.g., of the same family) based on identification using the fingerprint scanner 454. FIG. 16 illustrates another intelligent toilet 401' having a fingerprint scanner 454' located on a front central part of a top of the seat 432'. It is noted that fingerprint scanners can be located anywhere on the toilet. As another form of identification, the toilet can communicate with an external device 44, such as a user's smartphone, to indicate the user supplying, for example, a urine sample for testing. Other biometric data can be utilized to allow the toilets disclosed herein to identify the specific user, such as to store, track, and output data (e.g., data OHD) associated with the user's health.

Figure 17:
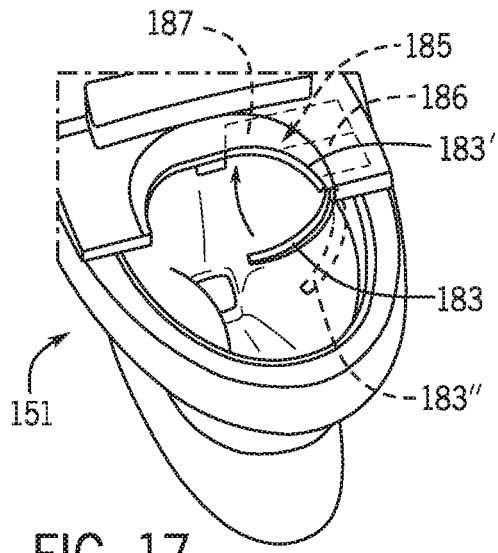
FIG. 17 is a perspective view of a toilet having a cleaning device in the seat system.
Figure 18:
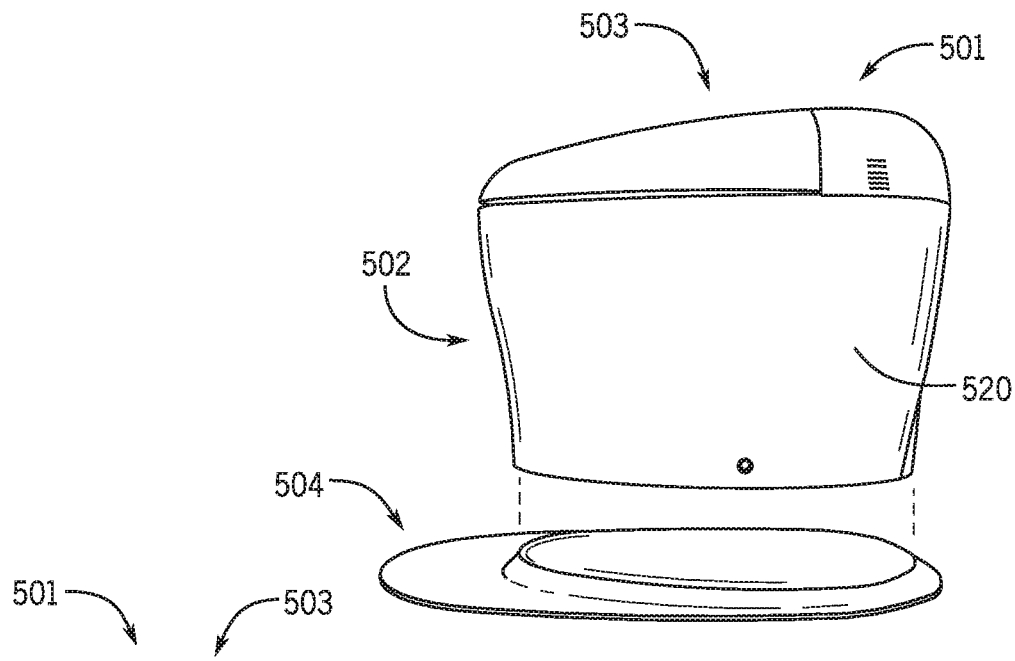
FIG. 18 is a side perspective view of another exemplary embodiment of an intelligent toilet.

As discussed above, the urine collection devices (e.g., the arms 133, 233, 333; the urine collection mechanism 433, etc.) can be cleaned or sanitized as required, such as after each use or upon demand by a user. Also discussed above, FIG. 8 illustrates the arm 133 being washed by a fluid F. This type of system can be incorporated into any of the other urine collection devices. FIG. 17 illustrates another type of cleaning device that can be employed in combination with or in place of the fluid washing device of FIG. 8. The toilet 151 illustrated in FIG. 17 includes an arm 183 that is configured similar to the arm 133, except located on the opposite side of the toilet 151. The arm 183 is rotatable between a first use position (identified with reference numeral 183), which can be for a first user (e.g., female users) of the toilet, a second use position (identified with reference numeral 183"), which can be for a second user (e.g., male users) of the toilet, and a non-use or cleaning position (identified with reference numeral 183'). The illustrated toilet 151 includes a cleaning device 185 that includes an ultraviolet (UV) light emitter 186 and a water sprayer 187, both of which are configured to clean or sanitize the arm 183' in the cleaning position. The UV light emitter 186 emits UV light when activated toward the arm 183' for a predetermined or inputted length of time. Similarly, the water sprayer 187 emits water when activated toward the arm 183' for a predetermined or inputted length of time. The water emitted from the water sprayer 187 can be heated, such as to a sanitizing temperature (e.g., at least 65° C. for at least 10 minutes; at least 70° C. for at least 5 minutes; etc.), or can include a cleaning chemical. The toilets disclosed herein can include one, both, or none of the UV light emitter 186 and the water sprayer 187.

Healthcare Toilet/Bidet

Returning to FIGS. 1 and 2, the intelligent toilet 1 includes a base 2 and a seat system 3. The base 2 includes the outer body 21, which serves as a housing by enclosing (e.g., surrounding, encapsulating, containing, etc.) other components of the toilet 1 (e.g., plumbing components, electrical components, mechanical components, etc.). The toilet 1 can provide additional features, such as contained within, external to, or on the body 21. For example, the toilet 1 can provide automatic opening and closing of the lid 33 and/or seat 31, such as through a motor driven by user detection of a sensor (e.g., proximity sensor) or other identifier, as well as flushing and other sanitation features. The toilet 1 can monitor lid orientation/position and provide alerts (e.g., ring tones) to the user based on an identification of the user through identifiers disclosed herein, as well as those facilitated by other intelligent bathroom device(s), data collected by such other device(s), or a user selection through the toilet 1 or such other device(s). The status of the intelligent toilet 1 can be transmitted to and/or displayed by other devices (e.g., the display 62, a smartphone, external device 44, etc.).

The toilet 1 can include a foot warmer 23 having a heating element that increases the temperature of the foot platform, in which the foot warmer 23 is integrated, for comfort of the user. The foot warmer 23 can include resistors (e.g., electric resistance wires, etc.), pipes carrying heated water, or any other suitable heating element to increase the temperature of the foot platform. The temperature can be selected based on an identification of the user, inputted by the user through a user input device 64 or other external device 44 (discussed below), such as other intelligent bathroom device(s), or by data collected by such other device(s). The user input device 64 can be a user interface integrated with the toilet 1 or a remote device (e.g., smartphone, tablet, remote control, etc.). The toilet 1 can collect biometric data or biological characteristics from the one or more users of the toilet 1, which can be used to improve service, such as by initiating the foot warmer 23 or aligning the lid 33 to a specific angle α (FIG. 2) or within a threshold range (e.g., angle α+/− another angle). Further, the toilet 1 can alert the user (e.g., ring tones) if the angle of the lid 33 is within a less ergonomic range (e.g., the range of angle β). This feature can be a posture reminder for the user.

The toilet 1 can include other features in the foot platform having the foot warmer 23. For example, a scale (e.g., weight sensor) can be included to measure/provide a weight, a body-mass-index (BMI), and/or a body fat of user. For example, the scale can include one or more pressure sensors or other suitable weight measuring instruments. The measured information can be displayed on a display 62, which can be located on the toilet 1 (e.g., on the foot platform, the outer body 21, etc.) or can be located remotely, such as on a wall display proximate the toilet 1. The measured information can be sent as data OHD to a smartphone or other user enabled device through a network 66 (FIG. 5), such as the internet, the network 43 (FIG. 3), or other suitable system. For example, the data OHD can be wirelessly communicated to a mobile application (e.g., using Wi-Fi or a Bluetooth connection). Regarding the BMI or body fat, a user can, for example, input the user's height, gender, and age into the mobile application, and the toilet 1 (e.g., microprocessor 452, controller 51, the scale, etc.) can analyze and indicate the current weight, body mass index and/or body fat of the user. Alternatively, the user's smartphone/device can calculate this information based on the data OHD communicated from the toilet 1.

In one or more embodiments, the scale platform includes a pressure sensor configured to detect the pressure of a user's foot on the platform. The pressure sensor can be activated (e.g., actuated) by mere presence of the user's foot on the foot warmer 23. The scale platform can additionally include temperature sensors, which activate heating of the foot warmer 23 in response to a sensed temperature of a user and/or of surrounding air.

In one or more embodiments, the scale platform is equipped with a heart rate sensor, such as disposed on the top surface of the foot platform (e.g., the scale). In this way, when a user has his feet on the platform, the heart rate sensor senses the user's heart rate and indicates the current heart rate to the user (e.g., through the toilet 1 and/or a connected smartphone or device).

The toilet 1 can include one or more than one speaker 63 (FIG. 5) integrated into the base 2, the seat assembly 3, and/or located remotely from the toilet 1 and connected through a network (e.g., the network 43). For example, one or more speakers 63 can be integrated with or embedded within the foot platform (e.g., scale, foot warmer, etc.) to alert the user regarding aspects such as posture, urine analysis, or other features of the toilet, as well as play music, such from a playlist on the user's smartphone.

Figure 3:
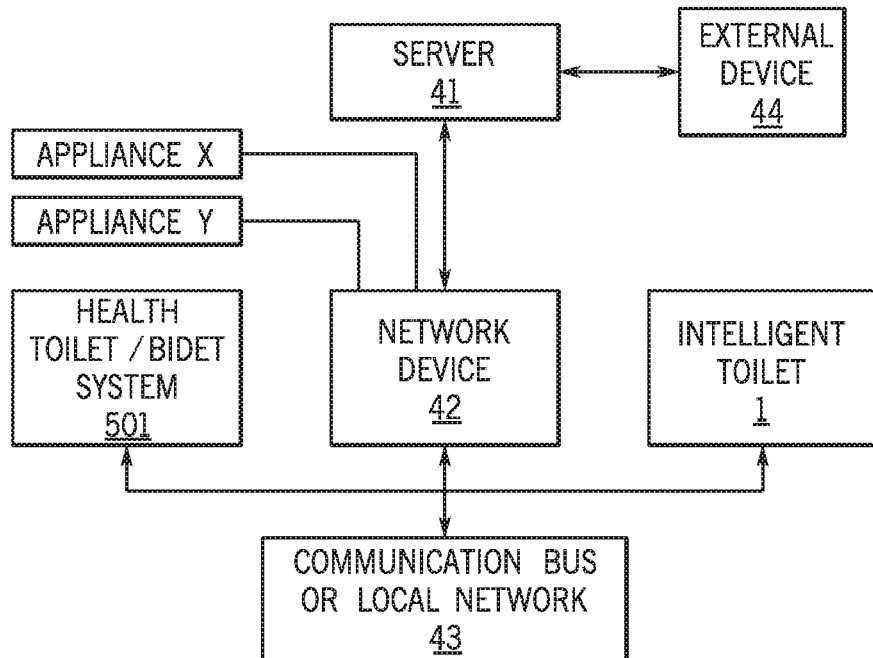
FIG. 3 is a block diagram of an exemplary embodiment of a communication network.

The toilet 1 can include a bidet wand or nozzle (e.g., the bidet wand 237) and, if provided, the toilet 1 can provide a predetermined temperature and/or a predetermined flow velocity of water from the bidet wand based on user identification and preference as discussed herein (e.g., a user selection on a mobile application). The status of the bidet wand 237 and water flow therefrom can be transmitted to and/or displayed on an external device (e.g., a mobile application). The arms (e.g., the arm 233) and/or bidet wand 237, if provided and moveable, can be moved to any position automatically by the toilet 1 based on user identification and preference or in response to an input from a user (e.g., external device). The bidet wand 237 can provide a variety of dispensing options for cleaning the user, which can be tailored to the specific user based on user identification. For example, the bidet wand can provide one or more dispensing options configured to use various amounts of water or power during the dispensing cycle. The bidet wand can any number of control options including user-customizable spray patterns, adjustable spray pressures, temperatures, and/or positions, each of which can be adjusted based on user data obtained by the communication network 43 (FIG. 3).

FIGS. 18-23 illustrate another exemplary embodiment of a health toilet/bidet system 501 that includes a toilet base 502, a seat assembly 503 coupled to the toilet base 502, and a platform 504 configured to rest on a floor and/or support the toilet base 502. The seat assembly 503 can be configured according to any of the others disclosed herein, such as having a seat, lid, and/or base. The platform 504 can include any of the features disclosed herein for other foot platforms, such as foot warmers, scales, speakers, sensors (e.g., heart rate sensors), etc.

Figure 19:
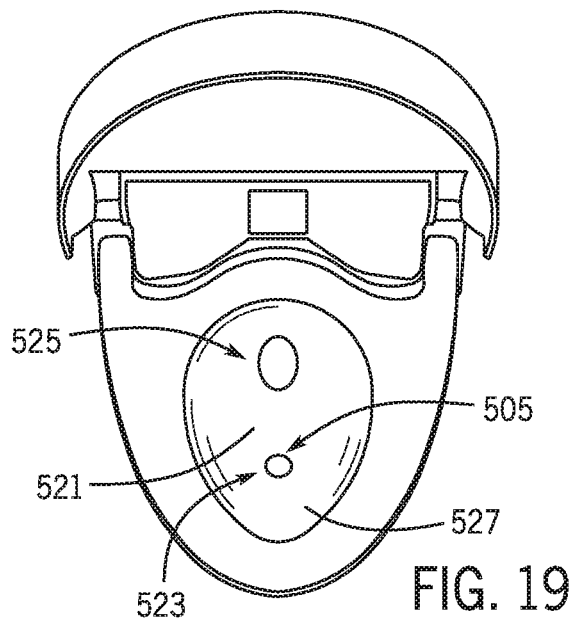
FIG. 19 is a top view of the toilet shown in FIG. 18.
Figure 20:
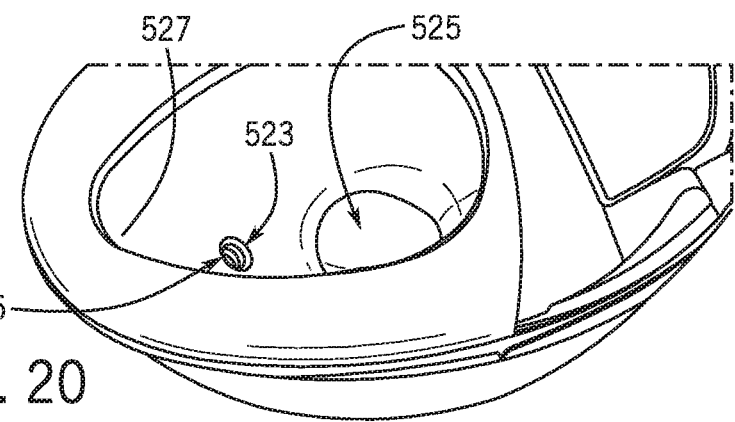
FIG. 20 is a perspective view of a portion of the toilet shown in FIG. 18.

The illustrated toilet base 502 includes a housing 520 surrounding a toilet bowl 521. As shown in FIGS. 19 and 20, disposed in an opening 523 of the bowl 521 is a urine collection system 505. The opening 523 is shown located in a centrally part of the bowl 521 laterally and between the outlet 525 of the bowl 521 and a front part 527 of the bowl 521. Studies show that this location is advantageous for capturing urine from the largest number of people.

Figure 21:
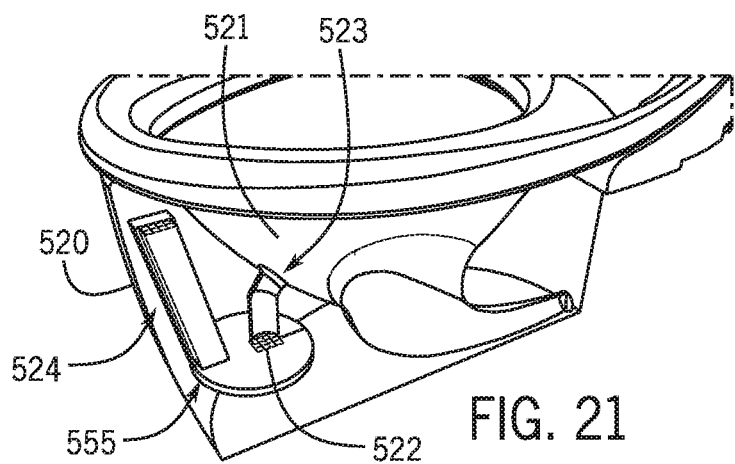
Figure 22:
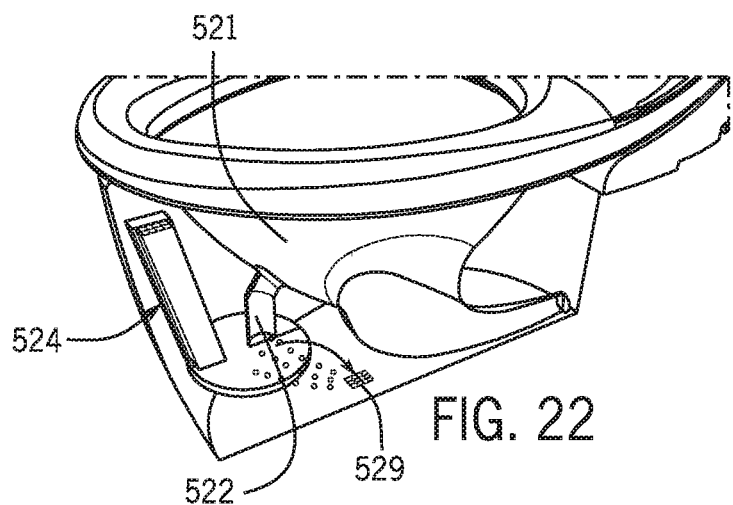
FIG. 22 is a partial cutaway perspective view of a portion of the toilet shown in FIG. 18.
Figure 23:
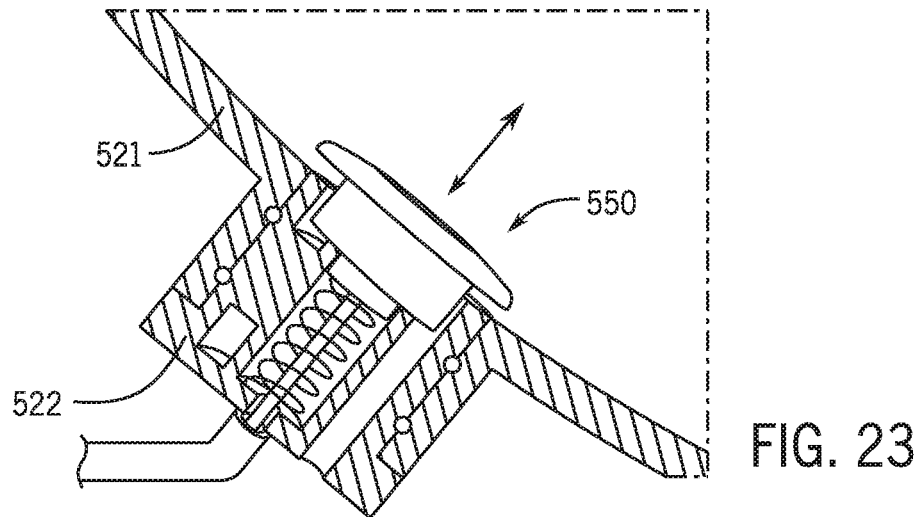
FIG. 23 is a partial cutaway perspective view of a portion of the toilet shown in FIG. 18.

As shown in FIGS. 21-23, a sleeve 522, which defines the opening 523 and extends away from the bowl 521, receives a valve 550 of the urine collection system 505. In an open position of the valve 550 (FIG. 23), urine is allowed to pass between the valve 550 and the sleeve 522 to capture a test sample, such as on a test strip, which can then be analyzed by an analyzer 555. In the closed position of the valve 550, urine is prevented from passing into the opening 523, as a head of the valve 550 closes off the opening 523 such as by covering it. The valve 550 is shown as spring loaded and can be moved using any suitable device (e.g., solenoid, motor, manually, etc.). The valve 550 can be controlled by a user, such as through a user interface of the toilet 501 and/or a smartphone/device. A plurality of test strips can be stored in a container 524 within the housing 520. The used test strip can be discarded through an outlet, such as the outlet 529 shown in FIG. 22. The toilet 501 can include a cleaner to clean the urine collection system 505, such as the cleaners discussed herein. As shown in FIG. 22, the urine collection system 505 is washed during a cleaning cycle.

Figure 24:
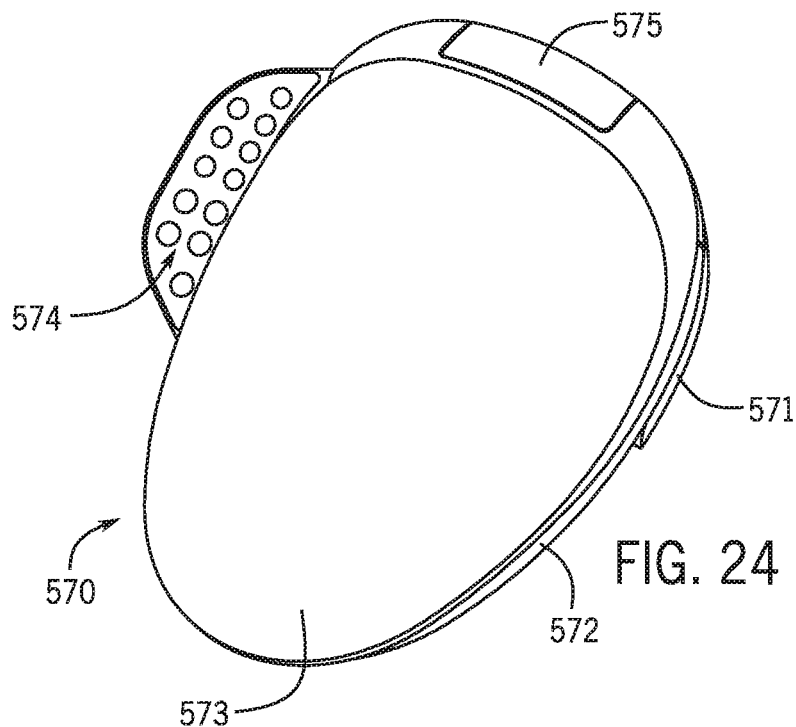
FIG. 24 is a perspective view of an exemplary embodiment of a smart bidet system.
Figure 25:
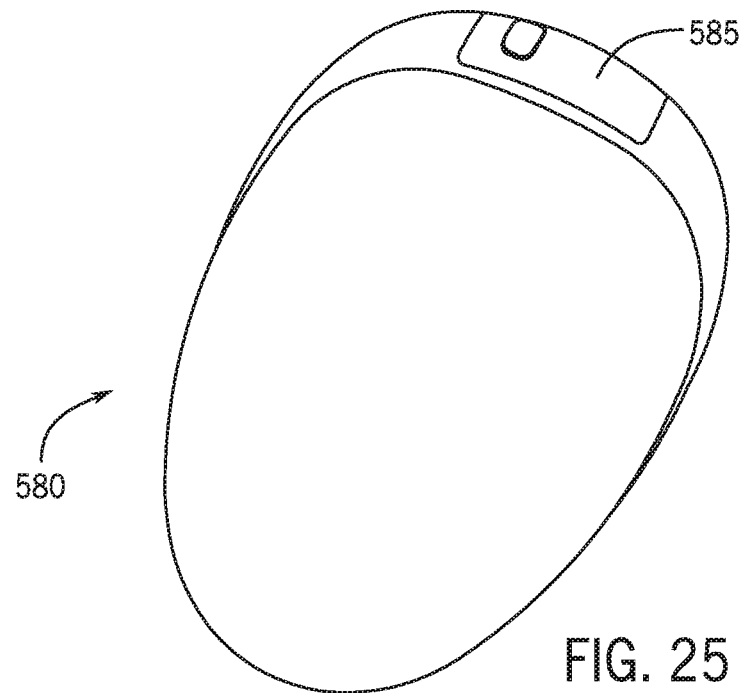
FIG. 25 is a perspective view of another exemplary embodiment of a smart bidet system.

Other types of toilets can be converted into bidet systems, such as by attaching a bidet seat system to the toilet. FIGS. 24 and 25 illustrate two examples of such bidet seat systems 570, 580. The system 570 includes a base 571, a seat 572, a lid 573, and a side panel 574. The side panel 574 is an (e.g., a user interface, communication interface 65, etc.) allowing a user to control all of the functions of the system 570 and/or the toilet to which the system 570 is coupled. The functions include, but are not limited to all of those discussed in this application. The system 570 can include a urine collector and analyzer 575, which can be configured according to any example discussed herein. The system 580 is similar to the system 570, except it lacks a side panel. Thus, the system 580 can include a urine collector and analyzer 585.

Personal (e.g., Female) Care Application

The toilets/bidets/systems disclosed herein can include one or more than one sensor 61 (FIG. 5) that can be configured to collect data on human waste. The sensor data can include or provide urinalyses or urine screening. The sensor data can include a pH level, an indication of the presence or absence of one or more ketones, an indication of the presence or absence hormones indicative of pregnancy, an indication of the presence or absence of blood cells or bacteria indicative of a urinary tract infection, an indication of the presence or absence of drugs, an indication of the presence or absence of a particular type of cells (e.g., cancer cells), and/or an indication of the presence or absence of other substances. The sensor 61 can include a light sensor (e.g., infrared light, laser, etc.) to test blood sugar levels or oxygen levels, which can be used to monitor diabetes. The sensor 61 can include a camera, which can collect data for stool samples. A control module, a home hub communication device, and/or an external device can be used to perform an image analysis on the stool samples.

The control module (e.g., controller 51) can send commands to a posture control module 52 to initiate a posture correction action (e.g., sound an alert and adjust the lid angle). The control module can send commands to a dispensing device (e.g., of the bidet) to command a specific type of spray (e.g., a specific spray pattern, pressure, or temperature). A dedicated remote (e.g., external device 44, wireless device 53, etc.), or a remote application on a smartphone/device, can receive user input for any of the commands for the control module.

The intelligent toilet 1, 501 can include a sensor, such as the sensor 61, which can be located anywhere on the toilet 1, 501 and can be configured to collect sensor data from one or more users. The sensor 61 can be an image collection device with a lens, such as a camera, or an image collection device with a charge coupled device (CCD), such as an integrated circuit, formed on a silicon surface forming light sensitive elements. The image collection device can collect images of the user. The image collection device can collect images for recognizing an image signature of a user such as the skin-tone or shape (e.g., bone density, outline, height, and/or weight) of the user. The image collection device can include a gesture sensor.

The sensor 61 can include a relative distance collection device such as a proximity sensor or a laser scanner. For example, the laser scanner can emit one or more laser pulses that reflect off of objects and are received by the laser scanner. The time of flight for the laser pulses indicates the distance to the objects. The proximity sensor may detect a presence of an object at a predetermined distance or within a predetermined distance range. For example, the proximity sensor can be coupled to the toilet, such as the lid 33 and can measure a distance between the user's back and the lid 33, such as where the proximity sensor is coupled.

The proximity sensor can emit and/or detect a beam of light (e.g., infrared light). Breaking the beam of light or interrupting the beam of light signals that a user is present on the toilet and/or on the foot platform. Breaking the beam of light can include placing a body part or object in the path of the beam of light so that the proximity sensor does not receive the beam of light. The beam of light can be located near the floor or base of the intelligent toilet such that the beam of light can be easily broken by a user's foot.

The sensor 61 can include a temperature mapping device, such as an infrared camera for detecting a heat signature of the user. The sensor 61 can include a retina scanner configured to scan the eyes of the user. The sensor 61 can include a fingerprint sensor or scanner (e.g., fingerprint scanner 454). The sensor 61 can be an audio sensor, such as a microphone.

The sensor 61 can communicate with the controller 51, display 62 and/or communication interface 65 to output a signal or data that describes when the intelligent toilet 1, 501 is in use. The sensor signal/data can be binary including one value to indicate the intelligent toilet 1, 501 is in use and another value to indicate the toilet is not in use.

The one or more sensors 61 can be incorporated into or with the seat assembly 3, the base 2, the housing 520, foot platform and/or other parts of the toilet. A weight sensor (e.g., pressure sensor) can be used to detect the user's weight when standing, or a rough estimate of the user's weight when seated on the toilet seat. The control module can calculate the weight of the user from the sensor data. The control module can determine a demographic type of user, such as man versus woman or adult versus child. The control module can identify the user, such as through biometric data. For example, in a household, weights of the people are distinct enough to recognize the identity of the individual users. The control module can learn the identities by measuring the weight of a known user. For example, the user can connect using a dedicated remote or a phone, and the control module can record a weight reading from the sensor(s) 61. The weight is stored by the control module, such as in a memory and/or drive unit, and when a subsequent user is seated, a subsequent reading is compared to the stored reading(s) to determine whether the identity of the user matches (e.g., is within a set tolerance of) any stored values. Any number of readings may be taken for any number of users.

An automated seat cover or lid, a seat, or a base or bowl of an intelligent toilet can include sensors, such as biometric sensors to detect biological characteristics or biometrics of the user(s). The sensor(s) can include a weight sensor configured to collect weight data for the user, a height sensor to determining the user's height, among other sensors, which the control module can use to calculate the user's BMI or body fat.

The biometric sensors can include a body composition sensor, which can measure muscle mass and/or body fat percentage using a bioelectrical impedance analysis. Alternatively, a body composition sensor can measure body water percentage contained in the cells and tissues using the bioelectrical impedance analysis, or bone mass using the bioelectrical impedance analysis. Changes in muscle or fat in certain parts of the body change the impedance of those parts of the body. The impedance can be detected by or communicated to the control module sending a low level electrical current through the user's body and measuring changes in the low level electrical current when it returns to a sensor and/or the control module. The current can enter and return from the user's body through, for example a seat, a seat lid or back, or a foot platform or the current may enter through one such component/element and return through another such component/element.

The biometric sensors can include a metabolic sensor that measures the basal metabolic rate (BMR) or minimal rate of energy per time expended by the user at rest while seated at the toiled. The BMR describes the calories needed by the body to rest.

The biometric sensors can include a photoplethysmogram (PPG) configured to optically obtain a volumetric measurement of an organ. The PPG may be configured to measure the heart rate of the user (e.g., through the skin), cardiovascular pulse wave velocity, respiration, or another characteristic of the user.

In one or more of these examples, the sensors detect biological characteristics, such as body composition, heart rate, temperature, and/or blood pressure of the user. The biometric sensors, taken alone or in combination with the weight sensor, can provide a user signature for identifying the user.

In addition to commands for the intelligent toilet, the control module can select an auxiliary command for an auxiliary device coordinated with the intelligent toilet based on the analysis of the sensor data. The auxiliary command can be selected for a particular user. The auxiliary command for the auxiliary device is based on the instruction from the user received at the user interface and the data displayed at the user interface includes status data for the auxiliary device, settings data for the auxiliary device, configuration data for the user, or type data for the auxiliary device. For example, the seat may be raised as a function of the identity of the user and/or time of day (e.g., gender, pattern of use, etc.).

The analysis of the sensor data may determine an instruction received at the user interface of the intelligent toilet, such as through gestures or other commands received by the sensors (e.g., voice commands). For example, the user may provide instructions to a music module (e.g., media player 54) to play music. Additionally or alternatively, the data from the external device 44 can impact or drive one or more than one setting of the toilet. In one example, weather data from a weather service is used to determine a temperature for the heater of the toilet seat.

Posture Reminder

FIG. 2 illustrates the toilet 1 having a posture detection and reminder mechanism, which is configured to detect a sitting posture of a user on the toilet 1, determine whether the detected posture is healthy, and provide an alert to the user in response to the result of the determination. The posture detection and reminder mechanism can include a distance sensor (e.g., sensor 61), a posture control module (e.g., posture module 52), and an alert (e.g., speaker 63). The distance sensor can be installed within or above the base 2 of the toilet 1 (e.g., the lid 33 of the seat assembly 3). The distance sensor can be installed at a predetermined height above the toilet 1 when the lid 33 is lifted to an open position. The distance sensor can be any type of distance proximity sensor (e.g., capacitive, displacement, Doppler effect, inductive, magnetic, optical, etc.) using any type of distance sensing technology to measure a distance between the distance sensor and the user's body. The distance sensor can be configured to send a distance signal representing the distance measurement to the posture control module.

The posture control module includes a processing circuit having a processor (e.g., microprocessor) and/or memory (FIG. 5). The control module can be configured to calculate an angle (e.g., angle α) between the spine and thighs of a user sitting on the toilet 1 by using the height of the distance sensor and horizontal distance from the user's spine. The posture control module can compare the calculated angle with a threshold value or threshold range to determine whether the user has a health posture. In some embodiments, the threshold range is approximately 45-55°. If the calculated angle is within the threshold range, then the posture control module sends a first posture control signal to the reminder module. In response to receiving the first posture control signal, the reminder module can, optionally, generate a first alert to indicate that the user currently has a healthy defecation posture. In some embodiments, the reminder module can play music in response to receiving the first posture control signal. The distance sensor can continue sending distance signals to the posture control module, such that when the calculated angle is not within the threshold range, the posture control module can send a second posture control signal to the reminder module. In response to receiving the second posture control signal indicating that the user is no longer within the healthy posture range, the reminder module can generate a second alert and/or cease playing music to indicate to the user of the change in posture. Alternatively, the first alert may be silence, while the second alert is an alarm or repeated ding. In this way, the user is incentivized to maintain a healthy posture while defecating.

Communication Network

FIG. 3 illustrates an exemplary embodiment of a communication network that communicates with a toilet/bidet system as disclosed herein. The illustrated communication network includes a server 41, a network device 42, a communication bus or local network 43, and an external device 44. The communication bus or local network 43 is connected to one or more health toilets and/or intelligent toilets. As shown, the communication bus or local network 43 is connected to the health toilet/bidet system 501 and the intelligent toilet 1. It is noted that the communication system can include additional, different, or fewer components. By way of example, the external device 44 can be a smart phone, a smart tablet, a computer, a smart watch, a remote control, or any other suitable device.

The server 41 can be a cloud device configured to communicate with multiple network devices 42 located in multiple locations (e.g., different homes or businesses). The server 41 can involve or implement a cloud service that coordinates and analyzes data from the multiple network devices 42 affiliates with multiple appliances (e.g., appliance X, appliance Y, etc.).

The network device 42 can be a standalone device (e.g., having a dedicated power supply, a speaker or smart speaker, and/or microphone) as a home hub communication device. Alternatively, the network device 42 can be integrated with one or more of the appliances.

Regarding the local analysis embodiments, the network device 42 receives data collected at appliance X and performs an analysis of the data to generate a command for appliance Y. The analysis can include determining an identity of the user of appliance X, a temporary state of the user of appliance X, or a command from the user of appliance X. An example of the identity of the user includes, but is not limited to an identifier for the user (e.g., username, user number, user code, etc.). Examples of the temporary state of the user include, but are not limited to drowsiness (e.g., sleep deprivation), complexion, sickness, intoxication, or mood. Examples of the command from the user include, but are not limited to turning on/off appliance Y or change a setting for appliance Y.

Regarding the remote analysis embodiments, the network device 42 can package or pre-process the data in a predetermined format and transmit the data to the server 41. The network device 42 can filter the data according to type, examples of which include, but are not limited to audio data, image data, position data, biometric data, ambient data, and/or other data types. The network device 42 can select a particular type of data to send to the server 41 based on the types of appliances associated with the network device 42. That is, the network device 42 can sort and select data collected at appliance X for use with appliance Y, according to the capabilities or configuration of appliance Y, and send the selected data to the server 41. In turn, the server 41 sends the selected data to appliance Y in response to the capabilities or configuration of appliance Y.

The network device 42 can package the data in a predetermined format and transmit the data to the server 41. The predetermined format may be specific to the type of data (e.g., a particular file format). In one example, the collected data includes voice commands and the predetermined format is an audio file. The predetermined format may be an audio encoding format (e.g., Moving Picture Experts Group (MPEG) standard, MPEG-2, mp3, wave file or other format).

Figure 4:
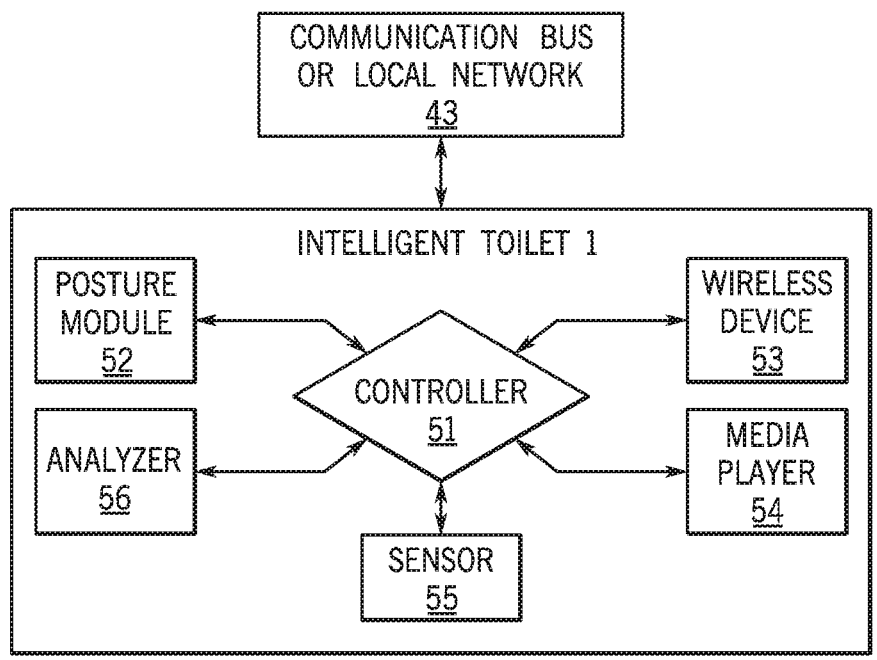
FIG. 4 is a flow chart of various features for a toilet, such as the toilet shown in FIG. 1.

FIG. 4 illustrates the intelligent toilet 1 receiving data through the communication bus or local network 43 and communicating with various features of the toilet 1 through an electronic controller 51. The illustrated toilet 1 includes a posture module 52, a wireless device 53 (e.g., a remote controller), a media player 54, a sensor 55 (e.g., vision sensor, IR sensor, proximity sensor, heating sensor, etc.), and an analyzer 56, all of which can be controlled operationally through the controller 51. For example, data can be entered into the external device 44 (FIG. 3) using, for example, a mobile application, which is communicated to the toilet 1 through the network 43, which in-turn, can activate or control operation of one or more of the various features of the toilet 1. As a specific example, a user can input a desired temperature of the foot warmer 23 into a mobile application of a smartphone, which in-turn is communicated to the controller 51 through the network 43, such that the controller 51 activates a heater to heat the foot warmer 23 to a temperature detected by a temperature sensor. Further, the controller 51 can communicate to the other devices through the network 43. For example, once the analyzer 56 has analyzed a urine sample from a user, the data OHD can be communicated to the user's smartphone through the network 43. It will be appreciated that other features shown in FIG. 4 and disclosed elsewhere in this application can be controlled in a similar manner to these examples, which are not limiting, but exemplary.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit and/or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

The above description is intended to be explanatory and, therefore, is non-limiting in nature. It should be noted that other variations may be made by those skilled in the art based on the principle of the disclosure of this application, which shall also be encompassed by the scope of the present invention as recited in the claims.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The terms "coupled," "connected," and the like, as used herein, mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

The construction and arrangement of the elements of the control systems/methods for toilets, bidets and the like, as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements, the position of elements may be reversed or otherwise varied, and the nature or number of discrete elements or positions may be altered or varied.

Additionally, the word "exemplary" is used to mean serving as an example, instance, or illustration. Any embodiment or design described herein as "exemplary" is not necessarily to be construed as preferred or advantageous over other embodiments or designs (and such term is not intended to connote that such embodiments are necessarily extraordinary or superlative examples). Rather, use of the word "exemplary" is intended to present concepts in a concrete manner. Accordingly, all such modifications are intended to be included within the scope of the present disclosure. Other substitutions, modifications, changes, and omissions may be made in the design, operating conditions, and arrangement of the preferred and other exemplary embodiments without departing from the scope of the appended claims.

Other substitutions, modifications, changes and omissions may also be made in the design, operating conditions and arrangement of the various exemplary embodiments without departing from the scope of the present invention. For example, any element (e.g., module, switch, etc.) disclosed in one embodiment may be incorporated or utilized with any other embodiment disclosed herein. Also, for example, the order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes and omissions may be made in the design, operating configuration, and arrangement of the preferred and other exemplary embodiments without departing from the scope of the appended claims.

What is claimed is:

1. An intelligent toilet, comprising:
   a toilet base having a bowl;
   a seat assembly comprising a seat; and
   a urine collection system at least partially integrated with the seat assembly, wherein the urine collection system includes:
      a mount including a receiving aperture, the receiving aperture configured to receive a test strip therethrough for capturing urine from a user; and
      an analyzer that is configured to test the urine from the user and provide health data of the user.

2. The intelligent toilet of claim 1, wherein the seat assembly comprises a base that is coupled to the toilet base, the urine collection system is integrated into the base of the seat assembly, the mount comprises an arm that is moveable within the bowl between a use position and a non-use position, and the receiving aperture is disposed in the arm.

3. The intelligent toilet of claim 2, further comprising a cleaning device that cleans at least a portion of the arm during a cleaning cycle, wherein the cleaning device comprises at least one of:
   a fluid emitter that emits a cleaning fluid over at least the portion of the arm during the cleaning cycle; and
   an ultraviolet light emitter that emits ultraviolet light onto at least the portion of the arm during the cleaning cycle.

4. The intelligent toilet of claim 3, wherein the arm is in the non-use position during the cleaning cycle, the arm nests with a recess in the base of the seat assembly in the non-use position, the cleaning device includes both the fluid emitter and the ultraviolet light emitter, and both the fluid emitter and the ultraviolet light emitter are located in the base of the seat assembly.

5. The intelligent toilet of claim 2, wherein the use position includes a first use position, which is predetermined for female users, and a second use position, which is predetermined for male users, and the intelligent toilet further comprises an identification system that identifies a gender of the user through at least one of a fingerprint, biometric data, and a user input from an external device.

6. The intelligent toilet of claim 5, further comprising:
a fingerprint scanner located on one of the toilet base and the seat assembly for identifying the user from the fingerprint; and
a controller configured to communicate with the fingerprint scanner, the analyzer, and the external device through a network so that the health data of the user can be received by the external device.

7. The intelligent toilet of claim 2, further comprising a bidet wand located adjacent to the arm, wherein the arm is telescopic.

8. The intelligent toilet of claim 2, further comprising a bidet wand that extends from a rear part of the bowl toward a central part of the bowl, wherein the arm extends from a side of the bowl toward the central part of the bowl.

9. The intelligent toilet of claim 1, wherein the seat includes a notch for detachably receiving the mount of the urine collection system, the mount includes the receiving aperture, and the mount complements the seat when the mount is coupled to the seat in the notch.

10. The intelligent toilet of claim 9, wherein the base of the seat assembly includes an inlet opening for receiving the test strip, and the analyzer is located in the base of the seat assembly.

11. The intelligent toilet of claim 1, further comprising a foot platform extending from a lower front of the toilet base, wherein the foot platform comprises at least one of a foot warmer comprising a heating element, a heart rate sensor that measures a heart rate of the user, or a scale that measures a weight of the user.

12. The intelligent toilet of claim 2, wherein the arm is rotatably coupled to the base, and wherein the receiving aperture is disposed in an end surface of a distal end of the arm relative to a pivot end of the arm.

13. The intelligent toilet of claim 11, further comprising all of the foot warmer, the heart rate sensor, and the scale, wherein the intelligent toilet further comprises a controller, including a microprocessor that controls operation of the foot warmer, receives a first input signal from the heart rate sensor in response to the measured heart rate, and receives a second input signal from the scale in response to the measured weight.

14. The intelligent toilet of claim 13, further comprising a display disposed on the toilet base or the platform, wherein the display is configured to display the measured heart rate and the measured weight in response to the first and second input signals.

15. The intelligent toilet of claim 13, wherein the controller communicates with an external device through a network so that the first and second input signals are received by the external device.

16. The intelligent toilet of claim 1, wherein the analyzer is configured to analyze urine captured on a test strip located in the seat assembly for collecting a sample of urine from a user.

17. The intelligent toilet of claim 1, further comprising:
a posture module comprising a sensor that measures and outputs a signal of a posture of the user when seated on the seat; and
a control module that receives the signal and compares the measured posture to a threshold range, so that a first posture control signal is emitted in response to the measured posture being within the threshold range and a second posture control signal is emitted in response to the measured posture being outside of the threshold range.

18. The intelligent toilet of claim 17, wherein the sensor is a distance sensor coupled to the lid so that in an open position of the lid, the distance sensor measures a distance to the user and communicates the distance to the control module.

19. The intelligent toilet of claim 18, further comprising a speaker that emits a first sound in response to the first posture control signal and emits a second sound in response to the second posture control signal, wherein the first sound is music and the second sound is an alert.

20. The intelligent toilet of claim 17, further comprising a speaker that is silent in response to the first posture control signal and emits a sound in response to the second posture control signal.

21. The intelligent toilet of claim 1, wherein the seat assembly comprises a base that couples the seat to the toilet base, wherein in the non-use position, the arm nests within a recess in a lower wall of the base.

22. The intelligent toilet of claim 9, wherein the notch comprises a recessed area in an upper surface of the seat.

* * * * *